United States Patent
Yadav et al.

(10) Patent No.: US 6,344,271 B1
(45) Date of Patent: Feb. 5, 2002

(54) MATERIALS AND PRODUCTS USING NANOSTRUCTURED NON-STOICHIOMETRIC SUBSTANCES

(75) Inventors: Tapesh Yadav; Ming Au; Bijan Miremadi; John Freim; Yuval Avniel; Roger Dirstine; John Alexander; Evan Franke, all of Longmont, CO (US)

(73) Assignee: NanoEnergy Corporation, Longmont, CO (US)

(*) Notice: Subject to any disclaimer, the term of this patent is extended or adjusted under 35 U.S.C. 154(b) by 0 days.

(21) Appl. No.: 09/274,517

(22) Filed: Mar. 23, 1999

Related U.S. Application Data

(60) Provisional application No. 60/107,318, filed on Nov. 6, 1998.

(51) Int. Cl.⁷ ............................................. B32B 5/16
(52) U.S. Cl. ...................................................... 428/402
(58) Field of Search .......................................... 428/402

(56) References Cited

U.S. PATENT DOCUMENTS

| | | | |
|---|---|---|---|
| 5,064,464 A | 11/1991 | Sawada et al. | 75/347 |
| 5,194,128 A | 3/1993 | Beaty et al. | 204/164 |
| 5,219,804 A | 6/1993 | Weimer et al. | 501/96 |
| 5,407,458 A | 4/1995 | König et al. | 75/255 |
| 5,447,708 A | 9/1995 | Helble et al. | 423/593 |
| 5,486,675 A | 1/1996 | Taylor et al. | 217/121.59 |
| 5,788,738 A | 8/1998 | Pirzada et al. | 75/331 |
| 5,866,975 A * | 2/1999 | Gartner et al. | 313/346 |
| 6,266,459 B1 * | 7/2001 | Walt et al. | 385/12 |
| 6,278,231 B1 * | 8/2001 | Iwasaki et al. | 313/310 |

OTHER PUBLICATIONS

Huang, et al., "Formation of Nanocrystalline B2 NiAl Through Cryomilling of Ni–50 at. % Al at 87 K", Nano-Structured Materials, 5:411–424 (1995).
Ishigaki, et al., "Compositional Modification of Titanium Carbide Powders by Induction Plasma Treatment", Journal of Materials Science 30: 883–890 (1995).

* cited by examiner

Primary Examiner—Hoa T. Le
(74) Attorney, Agent, or Firm—Stuart T. Langley; Hogan & Hartson LLP

(57) ABSTRACT

Nanoscale non-stoichiometric materials with unusual properties are disclosed. These materials offer a wide range of novel formulations for applications in catalysis, chemicals and fuels, electronics, electromagnetics, photonics, optics, sensors, electrochemical products, structural products, biomedical engineering, acoustics, composites, and other applications. Illustrative methods and processes are disclosed to highlight catalytic properties and electrical properties and to process these materials from powder or porous forms into dense forms and shapes. The invention includes a non-stoichiometric composition of a material, preferably in nanostructured form, for various applications including, but not limited to, methods to reduce the sintering temperature, the sintering time, or both.

45 Claims, 2 Drawing Sheets

MATERIALS AND PRODUCTS USING NANOSTRUCTURED NON-STOICHIOMETRIC SUBSTANCES

This invention claims the priority of provisional application number 60/107,318, filed Nov. 6, 1998, entitled "Materials and Products Using Nanostructured Non-stoichiometric Materials," which is incorporated herein by reference.

FIELD OF THE INVENTION

The invention relates to non-stoichiometric substances and more particularly to nanostructured non-stoichiometric substances and products incorporating such substances.

BACKGROUND OF THE INVENTION

Most compounds are prepared as stoichiometric compositions, and numerous methods of preparing substances for commercial use are motivated in objective to create stoichiometric compounds. For example, producers of titania fillers, copper oxide catalysts, titanate dielectrics, ferrite magnetics, carbide tooling products, tin oxide sensors, zinc sulfide phosphors, and gallium nitride electronics all seek stoichiometric compositions ($TiO_2$, $CuO$, $BaTiO_3$, $NiFe_2O_4$, $TiC$, $SnO_2$, $ZnS$, and $GaN$, respectively).

Those skilled in the art will note that conventional powders of oxides and other compounds, when exposed to reducing atmospheres (e.g. hydrogen, forming gas, ammonia, and others) over a period of time, are transformed to non-stoichiometric materials. However, the time and cost of doing this is very high because the inherent diffusion coefficients and gas-solid transport phenomena are slow. This has made it difficult and uneconomical to prepare and commercially apply stable non-stoichiometric forms of materials to useful applications.

Limited benefits of non-stoichiometric materials have been taught by others; for example, Sukovich and Hutcheson in U.S. Pat. No. 5,798,198 teach a non-stoichiometric ferrite carrier. Similarly, Menu in U.S. Pat. No. 5,750,188 teaches a method of forming a thin film of non-stoichiometric luminescent zinc oxide. The film is a result of a thermodynamically favored defect structure involving non-stoichiometric compositions where the non-stoichiometric deviation is in parts per million.

SUMMARY OF THE INVENTION

This invention includes several methods of making non-stoichiometric submicron and nanostructured materials and devices from both stoichiometric and non-stoichiometric precursors. This invention also includes methods of making stoichiometric materials and devices from non-stoichiometric precursors. In one aspect, the invention includes an improved sintering technique utilizing submicron non-stoichiometric powders. The invention also includes a variety of other applications for submicron non-stoichiometric materials, including catalysis, photonic devices, electrical devices and components, magnetic materials and devices, sensors, biomedical devices, electrochemical products, and energy and ion conductors.

In one aspect, this invention includes a variety of methods of producing a non-stoichiometric material. According to one method, a submicron powder of a stoichiometric material is transformed into a non-stoichiometric powder. The submicron powder may also be a nanopowder. If desired, the submicron non-stoichiometric powder may be sintered into a bulk substance.

According to a another method, a non-stoichiometric submicron material is produced by quenching a high-temperature vapor of a precursor material to produce a non-stoichiometric submicron powder. A vapor stream of the high temperature vapor flows from an inlet zone, and this stream is passed through a convergent means to channel the vapor stream through an area where flow is restricted by controlling the cross-section of the flowing stream. The vapor stream is channeled out of the flow restriction through a divergent means to an outlet pressure which is smaller than the inlet pressure. This quenches the vapor stream. The inlet and outlet pressures are maintained, creating a pressure differential between them. The pressure differential and the cross-section of the flow restriction are adapted to produce a supersonic flow of the vapor stream. This method may further comprise sintering the resulting powder.

According to yet another method, a submicron starting material comprising more than one element is provided. At least one of these elements is an electropositive element. A dopant element with valency different than the electropositive element is added, and the mixture is heated to a selected temperature, preferably greater than the solid state reaction temperature, for a time sufficient to allow intermingling of the dopant element and the given electropositive element.

According to still another method, two submicron powders are mixed in a ratio selected to produce a desired non-stoichiometric composition. The first submicron powder comprises a plurality of materials, and the second comprises a subset of those materials. The materials comprising the first submicron powder may be metallic, semi-metallic, non-metallic, or any combination thereof. The mixture is heated in a selected atmosphere to a temperature to produce a solid state reaction. The atmosphere may participate in the solid state reaction. This invention also includes the materials produced via the above methods and nanoscale materials produced from nanoscale starting materials via the above methods.

In another aspect, this invention includes a submicron non-stoichiometric material where the value for a selected physical property of the submicron non-stoichiometric material is greater than 10% different from that for a stoichiometric form of the submicron non-stoichiometric material. Alternately, the relative ratios of the components of the material differ by more than 1% from the stoichiometric values, preferably 2% from the stoichiometric values, and more preferably 5%. The material may be a nanomaterial or a nanopowder.

This invention also includes a submicron material wherein a domain size of the material is less than 500 nm, and the material is non-stoichiometric. Preferably, the domain size is less than 100 nm. Alternately, a domain size may be less than 5 times the mean free path of electrons in the given material, or the mean domain size may be less than or equal to a domain size below which the substance exhibits 10% or more change in at least one property when the domain size is changed by a factor of 2. The material may be a powder or a nanopowder.

In another aspect, this invention includes a method of determining the non-stoichiometry of a material. A stoichiometric form of the material and the material whose stoichiometry is to be ascertained (the "unknown" material) are heated separately in a reactive atmosphere to 0.5 times the melting point of the material. The weight change per unit sample weight for the unknown material is monitored. In addition, the weight change per unit sample weight of the unknown material is compared to the weight change per unit sample weight of the known material.

In another aspect, this invention includes a method of conducting combinatorial discovery of materials where non-stoichiometric forms of materials are used as precursors.

In another aspect, this invention includes a method of making a non-stoichiometric submicron device by fashioning a non-stoichiometric submicron material into a device. Alternately, a device is fashioned from a stoichiometric material and the stoichiometric material converted into a non-stoichiometric form. The stoichiometric material may be an electrochemical material, a photonic material, or a magnetic material. The non-stoichiometric material may be electroded; and the electrode may comprise a non-stoichiometric material. This invention also includes stoichiometric devices with non-stoichiometric electrodes. The devices and electrodes may incorporate submicron materials or nanomaterials.

In another aspect, this invention includes a method of producing a stoichiometric material from a non-stoichiometric powder. The powder is processed into the shape desired for a stoichiometric material and further processed to produce stoichiometric ratios among its components. This invention also includes a method of producing a stoichiometric device via the same method. The non-stoichiometric powders may be submicron powders or nanopowders.

In another aspect, this invention also includes an improved method of producing sintered materials. A submicron stoichiometric powder is formed into a green body. The green body is sintered at a selected densification rate and a selected temperature which are lower than those required to sinter larger, stoichiometric powders. This method may further comprise converting the sintered material to a stoichiometric form or stabilizing the non-stoichiometric sintered material by the addition of a protective coating, secondary phase, or stabilizer. In this method, the submicron non-stoichiometric powder may also be nanopowders.

This invention also includes a method of producing an improved catalyst. A nanopowder comprising indium tin oxide and alumina are pressed into pellets. The pellets are reduced in a reducing atmosphere to form a catalyst which can promote the formation of hydrogen from 12% methanol vapor at 250° C. This invention also includes the improved catalyst prepared by this method.

In another aspect, this invention includes a method of producing an improved photonic material. A high-temperature vapor of a precursor material is quenched from a gas stream comprising hydrogen and argon to produce a non-stoichiometric submicron powder such that the absorption of selected wavelengths is more than doubled with respect to that of a stoichiometric from of the precursor. In this method, the precursor material may be stoichiometric ITO; the selected wavelengths would be greater than 500 nm. In addition, this invention includes a improved non-stoichiometric photonic material produced by this process and exhibiting enhanced absorption of selected wavelengths of electromagnetic radiation in comparison to a stoichiometric form of the material.

In another aspect, this invention includes a method of producing an improved electric device. Titanium oxide nanopowders are heated in an ammonia atmosphere to produce a non-stoichiometric oxynitride of titanium. The resulting device may also be part of an electrical conductor. This invention also includes the improved electrical device produced by this method.

This invention also includes a variety of methods of making improved magnetic materials and devices. According to one method, a nickel zinc ferrite material is sintered to near theoretical density and heated in a reducing atmosphere at an elevated temperature such that the resulting material exhibits higher magnetic loss than the stoichiometric starting material. The atmosphere may comprise 5% H–95% Ar and the temperature may be 800° C.

According to another method, a mixture of two stoichiometric nanopowders is produced from manganese ferrite and nickel zinc ferrite powders. These two powders are pressed together, sintered, and wound. The method may further comprise pressing the two nanopowders with a binder, preferably 5% Duramax. This invention also includes the magnetic devices and materials produced by these methods.

In another aspect, this invention includes methods of making a non-stoichiometric resistor. In one method, the resistor is produced from a stoichiometric submicron material and transformed to a non-stoichiometric form. In another method, the resistor is produced from non-stoichiometric $SiC_x$ nanopowders. The nanopowders are sonicated in polyvinyl alcohol and screened printed on a alumina substrate. The resulting resistor element is to produce a resistor having a resistance less than 1 megaohm. Platinum or silver dopants may be added to the sonicated mixture. This invention also includes the improved resistors produced via these methods and arrays of resistors produced via these methods.

In another aspect, this invention also includes a method of producing an improved sensor device. A non-stoichiometric nanopowder is sonicated in a solvent to form a slurry. The slurry is brushed onto screen-printed electrodes and allowed to dry at to remove the solvent. A dissolved polymer may also be included in the slurry. The screen printed electrodes may be gold electrodes on an alumina substrate. The screen may be made from stainless steel mesh at least 8×10 inches in size, with a mesh count of 400, a wire diameter of 0.0007 inches, a bias of 45°, and a polymeric emulsion of 0.0002 inches.

In another aspect, this invention includes an improved sensor device prepared from a screen printable paste. A nanopowder and polymer are mechanically mixed; a screen printing vehicle is added to the mixture and further mechanically mixed. The mixture is milled and screen printed onto prepared electrodes. The paste is allowed to level and dry. This invention also includes the improved sensor devices produced by the above processes.

This invention, in a further aspect, includes a method of making an improved biomedical orthopedic device. A feed powder comprising a nonstoichiometric Ti—Ta—Nb— Zr alloy is milled under non-oxidizing conditions. The milled powder is mixed with a binder dissolved in a solvent and allowed to dry. The mixture is then pressed and incorporated into a biomedical device. This invention also includes a biomedical material comprising a non-stoichiometric submicron powder. In addition, this invention includes a biomedical material produced by this process wherein the powder is a nanopowder.

This invention, in another aspect, includes a method of preparing an improved electronic component. A non-stoichiometric nanoscale material is mixed with a screen printing material and the resulting paste screen-painted on an alumina substrate. The paste is wrapped up and dried on a heated plate and further screen printed with silver-palladium to form a conducting electrode. The silver-palladium is dried rapidly on a heated plate and the two films co-fired.

In another aspect, this invention includes an improved electrochemical material comprising a submicron nonstoichiometric material. The material has excess Gibbs free energy in comparison to larger grained materials. In addition, the material exhibits increased solute diffusion, lower phase transformation temperatures, and high compressive toughness.

In another aspect, this invention includes a method of making an improved energy and ion conducting device. A stoichiometric nanoscale starting powder is reduced at a temperature between 500° C. and 1200° C. in a forming gas to yield non-stoichiometric nanopowders. The powders are pressed into discs, sintered, and coated with a cermet paste comprising equal parts silver and a stoichiometric nanoscale form of the starting powder. Platinum leads are then attached to the cermet paste. Preferably, the cermet paste comprises silver and a non-stoichiometric version of the starting powder. The starting powder may be yttria-stabilized cubic zirconia, other metal oxides, a perovskite material, or another group IV oxide. This invention also includes the improved energy and ion conducting device produced by this method. In addition, it includes an ion and energy conducting device wherein the ion conductor is produced from nanostructured beta alumina, NASICON, lithium nitride, LISICON, silver iodide, $Rb_4Cu_{16}I_7Cl_{13}$, a polymer, or a perovskite.

In another aspect, this invention includes an improved dopant for semiconductor materials where the dopant comprises a non-stoichiometric nanocrystalline powder. The grain size of the non-stoichiometric nanocrystalline powder may be less than 80 nm, preferably 40 nm, and more preferably 10 nm. The non-stoichiometric nanocrystalline powder may include one or more materials selected from the group comprising $Ta_{2/3}O_{0.9}$, $Nb_{2/5}O_{0.74}$, $NiO_{0.98}$, $Mn_{1/2}O_{0.9}$, $Bi_{2/3}O_{0.45}$, $Cu_{1.9}O$, $TiO_{1.1}$, $SiO_{1.55}$, and $V_{2/5}O_{0.975}$.

BRIEF DESCRIPTION OF THE DRAWINGS

The invention is described with reference to the several figures of the drawing, in which.

DETAILED DESCRIPTION

Figure 1:
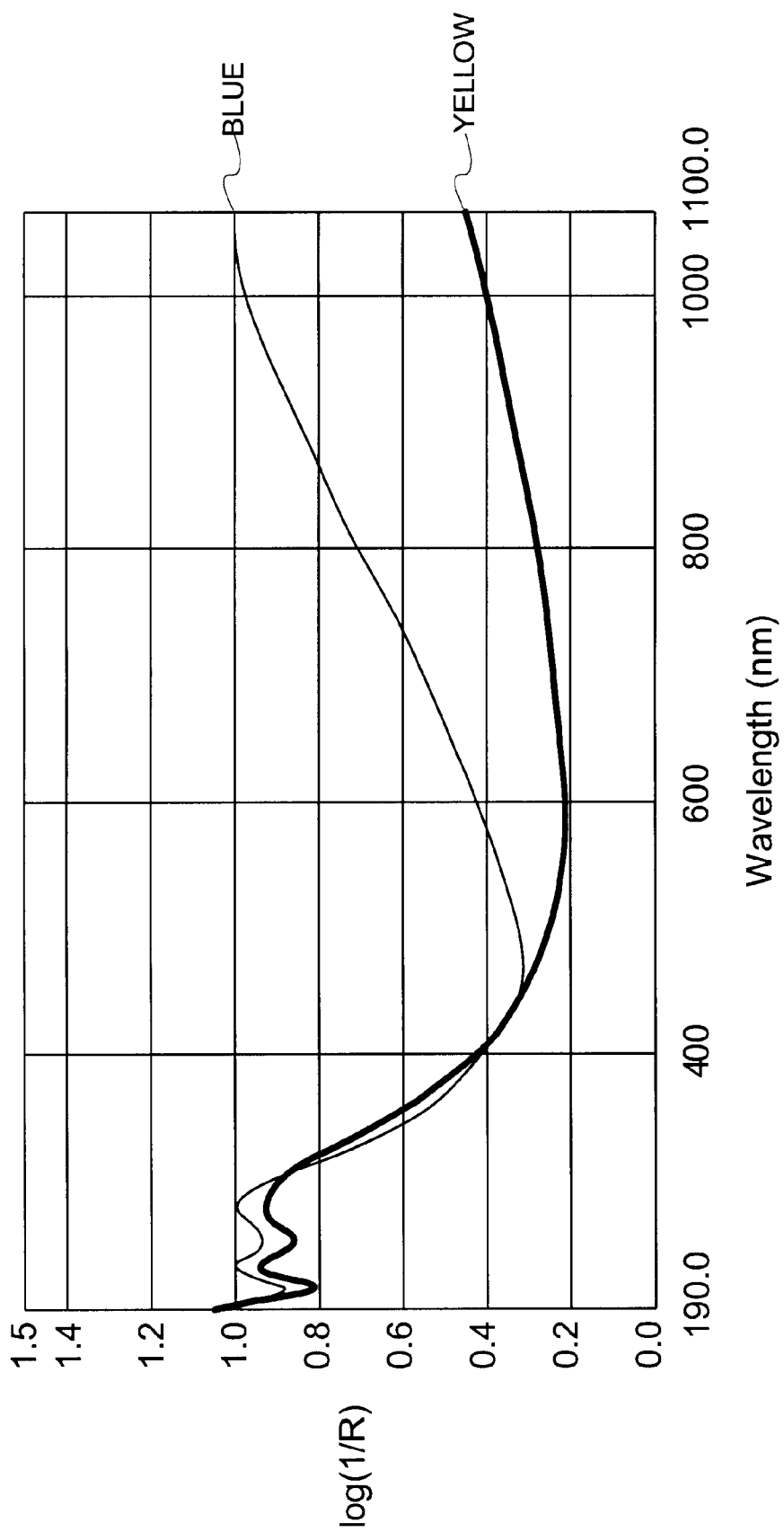
FIG. 1: UV-V is absorption spectra of stoichiometric indium tin oxide (yellow) and non-stoichiometric indium tin oxide (blue).

Non-stoichiometric substances in this invention are envisioned as substances that bridge between the artificial classification of substances—i.e. metals, alloys, oxides, carbides, nitrides, borides, sulfides, chalcogenides, silicides, etc. For example, while tin (Sn) is a metal, tin oxide ($SnO_2$) is an oxide ceramic. Non-stoichiometric tin oxide is then a form of a substance that transitions the properties of metallic tin to ceramic tin oxide. For example, non-stoichiometric tin oxides can be prepared with compositions such as $SnO_{0.04}$, $SnO_{0.14}$, $SnO_{0.24}$, $SnO_{0.34}$, $SnO_{0.44}$, $SnO_{0.54}$, $SnO_{0.64}$, $SnO_{0.74}$, $SnO_{0.84}$, and $SnO_{0.94}$. The physical, thermal, chemical, and other properties of tin and tin oxide are very different, and the properties of non-stoichiometric tin oxide are anticipated to be very different and unique when compared with both metallic tin and ceramic tin oxide. The presence of vacancies in $SnO_x$ is anticipated to lead to higher conductivities, novel catalytic properties, novel structural properties, novel magnetic properties, faster sintering, and other desirable commercial performance. A preferred embodiment is to use a submicron non-stoichiometric form. A more preferred embodiment is to use a nanoscale non-stoichiometric form. It is important to note that the non-stoichiometric form can be converted to a stoichiometric form if and when desired. Thus, the beneficial properties of non-stoichiometric forms can be utilized in some applications during processing, while leaving the flexibility for use of either a stoichiometric or a non-stoichiometric form in the final product.

Another illustration, without limiting the scope of this invention, is the non-metal boron and the ceramic boron nitride. In stoichiometric form, boron is B, and the ceramic boron nitride is BN. These two materials have very different molecular orbitals and different physical, thermal, chemical, optical, catalytic, structural, and other properties. Additionally, it is easier to process boron than boron nitride. Illustrative but not limiting forms of non-stoichiometric boron nitride include $BN_{0.025}$, $BN_{0.125}$, $BN_{0.225}$, $BN_{0.325}$, $BN_{0.425}$, $BN_{0.525}$, $BN_{0.625}$, $BN_{0.725}$, $BN_{0.825}$, $BN_{0.925}$. It is anticipated that nanoscale forms of these non-stoichiometric $BN_x$ will yield novel electrical and electronic properties, novel catalytic properties, novel structural properties, novel magnetic properties, faster sintering, and other desirable commercial performance. Once again, a preferred embodiment is to use a submicron non-stoichiometric form. A more preferred embodiment is to use a nanoscale non-stoichiometric form. Once again, it is important to note that the non-stoichiometric form can be converted to a stoichiometric form if and when desired. Thus, the beneficial properties of non-stoichiometric forms can be utilized in some applications during processing, while leaving the flexibility for use of either a stoichiometric or a non-stoichiometric form in the final product.

Yet another illustration, without limiting the scope of this invention, is metallic titanium and the ceramic titanium carbide. In stoichiometric form, metallic titanium is Ti, and ceramic titanium carbide is TiC. These two materials have very different molecular orbitals and different physical, thermal, chemical, optical, catalytic, structural, and other properties. It is easier to process metals than ceramics, and the ductilities of metals are very different than those of ceramics. Illustrative but not limiting forms of non-stoichiometric titanium carbide include $TiC_{0.05}$, $TiC_{0.15}$, $TiC_{0.25}$, $TiC_{0.35}$, $TiC_{0.45}$, $TiC_{0.55}$, $TiC_{0.65}$, $TiC_{0.75}$, $TiC_{0.85}$, $TiC_{0.95}$. It is anticipated that nanoscale forms of nonstoichiometric $TiC_x$ will yield novel electrical and electronic properties, novel catalytic properties, novel structural properties, novel magnetic properties, faster sintering, and other desirable commercial performance. Once again, a preferred embodiment is to use a submicron non-stoichiometric form. A more preferred embodiment is to use a nanoscale non-stoichiometric form. Once again, it is important to note that the non-stoichiometric form can be converted to a stoichiometric form if and when desired. Thus, the beneficial properties of non-stoichiometric forms can be utilized in some applications during processing, while leaving the flexibility for use of either a stoichiometric or a non-stoichiometric form in the final product.

A further illustration, without limiting the scope of this invention, is the nickel iron alloy and the ceramic nickel ferrite. In stoichiometric form, nickel iron alloy is NiFe, and ceramic nickel ferrite is $NiFe_2O_4$. These two materials have very different molecular orbitals and different physical, thermal, chemical, optical, catalytic, structural, and other properties. It is easier to process alloys than ceramics, and the ductilities of alloys are very different than those of ceramics. Illustrative but not limiting forms of non-stoichiometric nickel ferrite include $NiFe_2O_{3.91}$, $NiFe_2O_{3.71}$, $NiFe_2O_{3.51}$, $NiFe_2O_{3.31}$, $NiFe_2O_{3.11}$, $NiFe_2O_{2.91}$, $NiFe_2O_{2.71}$, $NiFe_2O_{2.51}$, $NiFe_2O_{2.31}$, $NiFe_2O_{2.11}$, $NiFe_2O_{1.91}$, $NiFe_2O_{1.71}$, $NiFe_2O_{1.51}$, $NiFe_2O_{1.31}$, $NiFe_2O_{1.11}$, $NiFe_2O_{0.91}$, $NiFe_2O_{0.71}$, $NiFe_2O_{0.51}$, $NiFe_2O_{0.31}$, $NiFe_2O_{0.11}$, $NiFe_{1.8}O_4$, $NiFe_{0.8}O_4$, $Ni_{0.9}Fe_2O_{3.9}$, $Ni_{0.9}Fe_2O_4$, and $Ni_{0.4}Fe_2O_4$. It is anticipated that nanoscale forms of non-stoichiometric nickel ferrite will yield novel electrical and electronic properties, novel catalytic properties, novel structural properties, novel magnetic properties, faster sintering, and other desirable commercial performance. Once again, a preferred embodiment is to use a submicron non-stoichiometric form. A more preferred embodiment is to use a nanoscale non-stoichiometric form. Once again, it is important to note that the non-stoichiometric form can be converted to a stoichiometric form if and when desired. Thus, the beneficial properties of non-stoichiometric forms can be utilized in some applications during processing, while leaving the flexibility for use of either a stoichiometric or a non-stoichiometric form in the final product.

Nanostructured materials have small grain sizes and high interfacial areas. Nanostructured materials can be prepared by methods such as those taught by us in commonly assigned U.S. Pat. No. 5,788,738 and others such as U.S. Pat. Nos. 5,486,675, 5,447,708, 5,407,458, 5,219,804, 5,194,128, 5,064,464, all of which are incorporated herein by reference. Relatively high surface area and small grain size makes nanopowders commercially suitable for processing into non-stoichiometric forms.

The material compositions to be used in the presently claimed invention are nanostructured non-stoichiometric substances, i.e. materials whose domain size have been engineered to sub-micron levels, preferably to nanoscale levels (<100 nm) where domain confinement effects become observable, modifying the properties of the materials. The scope of this invention excludes non-stoichiometry that results from thermodynamically favored defect structure.

Nanostructured materials (nanomaterials) are a novel class of materials whose distinguishing feature is that their average grain size or other domain size is within a size range where a variety of confinement effects dramatically change the properties of the material. A property will be altered when the entity or mechanism responsible for that property is confined within a space smaller than the critical length associated with that entity or mechanism. Some illustrations of such properties include but are not limited to electrical conductivity, dielectric constant, dielectric strength, dielectric loss, polarization, permittivity, critical current, superconductivity, piezoelectricity, mean free path, curie temperature, critical magnetic field, permeability, coercive force, magnetostriction, magnetoresistance, hall coefficient, BHmax, critical temperature, melting point, boiling point, sublimation point, phase transformation conditions, vapor pressure, anisotropy, adhesion, density, hardness, ductility, elasticity, porosity, strength, toughness, surface roughness, coefficient of thermal expansion, thermal conductivity, specific heat, latent heat, refractive index, absorptivity, emissivity, dispersivity, scattering, polarization, acidity, basicity, catalysis, reactivity, energy density, activation energy, free energy, entropy, frequency factor, environmental benignity, bioactivity, biocompatibility, and thermal and pressure coefficients of properties. The importance of nanostructured materials to this invention can be illustrated by considering the example of the mean free path of electrons, which is a key determinant of a material's resistivity. The mean free path in conventional materials and resistivity are related by:

$$\rho = m v_E / n q^2 \lambda \qquad (1)$$

where,

ρ: resistivity m: mass of electron $V_E$: Fermi energy n: number of free electrons per unit volume in material q: charge of electron λ: mean free path of electron This equation assumes that the resistivity in the material is determined in part by the mean free path of electrons and that the electrons have a free path in the bulk. In nanostructured materials, the domain size is confined to dimensions less than the mean free path and the electron meets the interface of the domain before it transverses a path equal to the mean free path. Thus, if the material's domain size is confined to a size less than the mean free path, this equation is no longer valid. In a simplistic model, one could replace λ with the domain size, but that replacement ignores the fact that confinement can also affect "n" and other fundamental properties. This insight suggests that unusual properties may be expected from devices prepared from materials with a domain size less than the mean free path of electrons.

While the above argument is discussed in light of mean free path, it is important to note that the domain confinement effect can be observed even when the domain size is somewhat larger than the mean free path because: (a) "mean" free path is a statistical number reflecting a mean of path lengths statistically observed in a given material, and (b) in very finely divided materials, the interface volume is significant and all the free electrons do not see the same space; electrons closer to the interface interact differently than those localized in the center of the domain.

The significance of using nanostructured materials can be further appreciated if the conductivity of semiconducting oxides is considered as shown in the equation for conductivity from hopping mechanism:

$$\sigma = P_a P_b 2 e^2 / C k T v [\exp(-q/kT)] \qquad (2)$$

where,

σ: conductivity $P_a$, $P_b$: probabilities that neighboring sites are occupied by desirable cations e: electronic charge n: frequency factor k: Boltzmann's constant T: temperature q: activation energy c: unit cell dimension v: hopping velocity The frequency factor and activation energy are a strong function of the microstructure confinement and non-stoichiometry; therefore, the conductivity of the same material can be very different in nanostructured non-stoichiometric form when compared with naturally occurring bulk crystal form of the substance.

As the phrase is used herein, "nanostructured materials" are considered to be materials with a domain size less than 5 times the mean free path of electrons in the given material, preferably less than the mean free path of electrons. Alternatively, the domain size may be less than 500 nanometers, and preferably less than 100 nanometers. Nanostructured materials also include substances with a mean domain size less than or equal to the domain size below which the substance exhibits 10% or more change in at least one property of the said substance when the domain size is changed by a factor of 2, everything else remaining the same. Furthermore, the term nanostructured materials incorporates zero dimensional, one dimensional, two dimensional, and three dimensional materials.

Nanopowders in this invention are nanostructured materials wherein the domain size is the powder's grain size. For the scope of the invention, the term nanopowders includes powders with an aspect ratio different than one, and more specifically powders that satisfy the relation: $10^0 <$ aspect ratio $< 10^6$.

Submicron materials in this disclosure are materials with mean grain size less than 1 micrometer.

Non-stoichiometric materials are metastable materials which have a composition that is different than that required for stoichiometric bonding between two or more elements. For example, stoichiometric titania can be represented as $TiO_2$ while non-stoichiometric titania can be represented as $TiO_{2-x}$ ($TiO_{1.8}$ and $TiO_{1.3}$ would be two specific examples of non-stoichiometric titania). Stoichiometric bonding between two or more elements indicates that charge balance is achieved among the said elements. In general, a stoichiometric material is given by:

$$M_n Z_p \qquad (3)$$

where, Z can be any element from the p, d, and f groups of the periodic table (illustrations include: C, O, N, B, S, H, Se, Te, In, Sb, Al, Ni, F, P, Cl, Br, I, Si, and Ge). M can be any element that can lower its free energy by chemically bonding with Z (illustrations include: Ti, Mn, Fe, Ni, Zn, Cu, Sr, Y, Zr, Ta, W, Sc, V, Co, In, Li, Hf, Nb, Mo, Sn, Sb, Al, Ce, Pr, Be, Np, Pa, Gd, Dy, Os, Pt, Pd, Ag, Eu, Er, Yb, Ba, Ga, Cs, Na, K, Mg, Pm, Pr, Ni, Bi, Tl, Ir, Rb, Ca, La, Ac, Re, Hg, Cd, As, Th, Nd, Tb, Md, and Au), where n and p, integers for stoichiometric bonding between M and Z, are greater than or equal to 1.

A non-stoichiometric form of the same material may then be given by:

$$M_{n-x} Z_{p-y} \qquad (4)$$

where $0<x<n$ and $0<y<p$.

An alternative representation of a non-stoichiometric material is $M_{n/p}, Z_{1-x}$, where $0<x<1$. In this invention, the preferred range includes $0.01<x<0.99$, preferably $0.02<x<0.98$, and more preferably $0.05<x<0.95$.

Empirical methods may also be used to determine whether a material is non-stoichiometric. Some embodiments of such methods are as follows:

a. Heat a stoichiometric form of the material and the material being evaluated for non-stoichiometry separately in a reactive atmosphere (e.g., oxygen, if oxygen non-stoichiometry is being ascertained) to 0.5 times the melting point of the material; monitor the weight change per unit sample weight. The material being evaluated is non-stoichiometric if its weight change per unit sample weight is greater than either 1% of the weight of the sample or 25% of the weight change in the sample of stoichiometric form.

b. Alternatively, perform a quantitative elemental analysis on the material; if the relative ratio of the elements yields an "x" that is not an integer (and the relative ratio deviates by more than 1%, preferably more than 2% and more preferably by more than 5%), the material is non-stoichiometric.

c. Alternatively, measure the properties of the material in the ideal stoichiometric form and compare this with the substance being evaluated for non-stoichiometry; if any property of the material, or the temperature coefficient of any property varies by more than 10% between the two substances, everything else remaining the same, the substance being evaluated is non-stoichiometric.

These empirical methods will not work universally and may give misleading results because some materials decompose with heating, and analytical techniques are prone to statistical errors. These empirical methods should not be considered limiting and other methods of establishing "x" fall within the scope of the invention.

In the $M_{n-x} Z_{p-y}$ representation discussed above, non-stoichiometric materials may have more than one "M," more than one "Z," or both. In this case, the representation can be $II_{Ij}(M_{I,ni-xi} Z_{j,pj,yj})$ where $II_{I,j}$ represents a multiplicity in i and j. A material is then non-stoichiometric if the relative ratio of any M or any Z or any combination is different by more than 2.5% than what is needed for theoretical bonding between the said elements. Some illustrations of this, without limiting the scope of the invention, would be non-stoichiometric compositions such as $BaTiO_{3-x}$, $Ba_{1-x}TiO_3$, $NiFe_2O_{3-x}$, $Ni_{1-x}Fe_2O_3$, $NiFe_2O_3N_{1-x}$, $PbZrTiO_{3-x}$, $TiCN_{1-x}$, and $TiC_{1-x}N$. It is also important to note that, for the scope of this invention, non-stoichiometric substances include substances produced when one or more of Z and/or M in $II_{Ij}(M_{I,ni-xi} Z_{j,pj,yj})$ is replaced partially or completely with additional elements, i.e., $Z_S$ or $M_s$. An example of this would be stoichiometric $MnFe_2O_4$, which, after processing, becomes $MnFe_2O_{3.5}N_{0.1}$ or $MnFe_2O_{3.1}B_{0.3}$. Another example of this is stoichiometric $TiB_2$ which after processing becomes $TiB_{1.5}N_{0.3}$ or $TiB_{1.1}C_{0.2}$.

It is important to note that all naturally produced and artificially produced materials have defects because defects are thermodynamically favored. Such thermodynamically favored defects can lead to small amounts of inherent non-stoichiometry in substances. The presently claimed non-stoichiometric materials differ from such naturally produced and artificially produced substances in the following:

This invention excludes from its scope the non-stoichiometry that naturally results from the randomly occurring thermodynamic defects in a bulk crystal of the theoretical stoichiometry which are typically on the order of a few hundred parts per million. Preferred levels of non-stoichiometry according to the invention are those which significantly exceed equilibrium levels. Alternatively, the preferred ranges include $0.01<x<0.99$, preferably $0.02<x<0.98$, and more preferably $0.05<x<0.95$.

This invention teaches the methods for engineering unusual non-stoichiometric compositions, and provides motivation to harness their unusual properties. The invention stabilizes and makes non-stoichiometry commercially attractive by engineering nanostructure in the non-stoichiometric material. It should be noted that nanostructured non-stoichiometric substances are anticipated to have interfacial stresses that play an important role in determining the unique properties and unusual thermodynamic nature of these substances, thereby yielding materials with unprecedented compositions of matter and performance.

In the presently claimed invention, the scope of the invention includes nanostructured materials with a domain size less than 5 times the mean free path of electrons in the given material, preferably less than the mean free path of electrons. In the event that it is difficult to theoretically compute the mean free path of the non-stoichiometric material under consideration, it is recommended that the domain size be less than 500 nanometers, preferably less than 100 nanometers. If it is difficult to measure the grain size or the grain size changes during the production or use of the device, the scope of the invention includes nonstoichiometric materials with a domain size that exhibit 10% or more change in at least one property of the said substance when the domain size is changed by a factor of 2, everything else remaining same.

A very wide range of material properties and product performance can be engineered by the practice of the invention. For example, unusual or improved electrical, electronic, magnetic, optical, electrochemical, chemical, catalytic, thermal, structural, biomedical, surface properties, and combinations thereof can be obtained or varied over a wider range using nanostructured non-stoichiometric substances than is possible using prior art stoichiometric substances. Such benefits can motivate use of these materials in pellet or film type or multilayer type devices and products.

Nanostructured non-stoichiometric substances can be used as fillers to lower or raise the effective resistivity, effective permittivity, and effective permeability of a polymer or ceramic matrix. While these effects are present at lower loadings, they are expected to be most pronounced for filler loadings at or above the percolation limit of the filler in the matrix (i.e. at loadings sufficiently high that electrical continuity exists between the filler particles). Other electrical properties which could potentially be engineered include breakdown voltage, skin depth, curie temperature, temperature coefficient of electrical property, voltage coefficient of electrical property, dissipation factor, work function, band gap, electromagnetic shielding effectiveness and degree of radiation hardness. Nanostructured non-stoichiometric fillers can also be used to engineer magnetic properties such as the coercivity, BH product, hysteresis, and shape of the BH curve of a matrix. Even when non-stoichiometric substances are used in monolithic form, these unique electrical, magnetic, and electronic properties hold significant commercial interest.

Other important characteristics of an optical material are its refractive index and transmission and reflection characteristics. Nanostructured non-stoichiometric substances can be used to produce composites with refractive indices engineered for a particular application. Gradient lenses produced from nanostructured non-stoichiometric composites are anticipated to reduce or eliminate the need for polishing lenses. The use of nanostructured non-stoichiometric substances are anticipated to also help filter specific wavelengths. Furthermore, an expected advantage of nanostructured non-stoichiometric substances in optical applications is their enhanced transparency because the domain size of nanostructured fillers ranges from about the same as to more than an order of magnitude less than visible wavelengths of light. Photonic applications where specific wavelengths of light are processed are anticipated to utilize the unique optical properties of non-stoichiometric substances.

The high surface area and small grain size of non-stoichiometric substances and their composites make them excellent candidates for chemical and electrochemical applications. When used to form electrodes for electrochemical devices, these materials are expected to significantly improve performance, for example, by increasing power density in batteries and reducing minimum operating temperatures for sensors. Nanostructured non-stoichiometric substances are also expected to modify the chemical properties of composites. These unique non-stoichiometric substances are anticipated to be catalytically more active and to provide more interface area for interacting with diffusive species. They are anticipated to provide the materials needed in our commonly assigned patent application Ser. No. 09/165,439 on a method and process for transforming chemical species which utilizes electromagnetic fields, and which is incorporated by reference herein. Such substances are anticipated to also modify chemical stability and mobility of diffusing gases. Furthermore, nanostructured non-stoichiometric substances are anticipated to enhance the chemical properties of propellants and fuels or safety during storage and transportation or both.

Many nanostructured non-stoichiometric substances have a domain size comparable to the typical mean free path of phonons at moderate temperatures. These non-stoichiometric substances are anticipated to have dramatic effects on the thermal conductivity and thermal shock resistance of matrices and products into which they are incorporated. Potential applications include fluids used for heat transfer.

Nanostructured non-stoichiometric substances - which may be utilized in coated and uncoated form-and composites derived thereof are also expected to have significant value in biomedical applications for both humans and animals. For example, the small size of nanostructured non-stoichiometric substances will make them readily transportable through pores and capillaries. This suggests that the non-stoichiometric substances will be of use in developing novel time-release drugs and methods of administration and delivery of drugs, markers, and medical materials. A polymer coating can be utilized either to make water-insoluble fillers into a form that is water soluble, or to make water-soluble fillers into a form that is water insoluble. A polymer coating on the filler may also be utilized as a means to time drug-release from a nanoparticle. A polymer coating may further be used to enable selective filtering, transfer, capture, and removal of species and molecules from blood into the nanoparticle.

The invention can be used to prepare propellants and fuels that are safer to store, transport, process, and use. The non-stoichiometry can also provide increased energy density or oxidant or both.

The invention can be used to produce superior or more affordable catalysts for the synthesis of currently used and novel organic compounds, inorganic compounds, organo-metallic compounds, pharmaceuticals, polymers, petrochemicals, reagents, metallurgical products, and combinations thereof. The invention can also be used to produce superior or more affordable catalysts for environmental and other applications that currently or in the future can benefit from catalysis. Similarly, the invention can be used to produce superior or more affordable phosphors for monochromatic and color display applications.

A nanoparticulate non-stoichiometric filler for biomedical operations might be a carrier or support for a drug of interest, participate in the drug's functioning, or might even be the drug itself. Possible administration routes include oral, topical, and injection routes. Nanoparticulates and nano-composites are anticipated to also have utility as markers or as carriers for markers. Their unique properties, including high mobility and unusual physical properties, make them particularly well-adapted for such tasks.

In some examples of biomedical functions, magnetic non-stoichiometric nanoparticles such as ferrites may be utilized to carry drugs to a region of interest, where the particles may then be concentrated using a magnetic field. Photocatalytic non-stoichiometric nanoparticles can be utilized to carry drugs to a region of interest and then photo-activated. Thermally sensitive non-stoichiometric nanoparticles can similarly be utilized to transport drugs or markers or species of interest and then thermally activated in the region of interest. Radioactive non-stoichiometric nanoparticulate fillers are anticipated to have utility for chemotherapy. Nanoparticles suitably doped with genetic, cultured, or other biologically active materials may be utilized in a similar manner to deliver therapy in target areas. Nanocomposite particles may be used to assist in concentrating the particle and then providing therapeutic action. To illustrate, magnetic and photocatalytic nanoparticles may be formed into a composite, administered to a patient, concentrated in area of interest using a magnetic field, and finally activated using photons directed to the concentrated particles. As markers, coated or uncoated non-stoichiometric nanoparticulate fillers may be used for diagnosis of medical conditions. For example, fillers may be concentrated in a region of the body where they may be viewed by magnetic resonance imaging or other techniques. In all of these applications, the possibility exists that nanoparticulates can be released into the body in a controlled fashion over a long time period, by implanting a nanocomposite material having a bioabsorbable matrix, which slowly dissolves in the body and releases its embedded filler.

Other benefits disclosed in our U.S. patent application Ser. No. 09/083,893 on nanostructured fillers, and which is incorporated by reference herein, are applicable to the non-stoichiometric materials of the present invention.

Without limiting the scope of this invention, some exemplary methods which can be used to produce non-stoichiometric materials, are Method 1: Start with submicron powders, preferably nanopowders. Transform the powders into a non-stoichiometric form by one or more of the following techniques—heating in inert atmosphere, heating in oxidizing atmosphere, heating in reducing atmosphere, solvent extraction, chemical reaction, electrochemical transformation, electromagnetic field treatment, ion beam treatment, electron beam treatment, photonic treatment, rapid quench, plasma treatment, nuclear radiation, supercritical phase treatment, biological treatment, or a combination of one or more techniques. Utilize the non-stoichiometric material so obtained. It may be desirable to sinter the non-stoichiometric powders into a solid. It may further be desirable to reconvert the non-stoichiometric material to a stoichiometric form.

Method 2: Produce non-stoichiometric powders, preferably nanopowders directly with techniques such as those taught in commonly assigned U.S. Pat. No. 5,788,738. Utilize the non-stoichiometric powders so obtained. For example, sinter and process them as appropriate. Finally, if desired, convert them to stoichiometric form.

Method 3: Mix nanoscale powders of a material and at least one of its components in a desired ratio and heat the combination in an inert or other appropriate atmosphere to a temperature that completes the solid state reaction. The material may comprise metallic, semi-metallic, or non-metallic components, or any combination thereof. It may be possible to heat the materials in a reactive atmosphere to further control the ratio desired among the components in the final product. Utilize the non-stoichiometric substance so obtained.

Method 4: Add a dopant element with a valency different than one of the electropositive constituents in the substance in which non-stoichiometry is to be engineered. Heat the mix to a temperature greater than the solid state reaction temperature for a time that enables intermingling of the dopant element and the primary electropositive constituent. The objective in this procedure is to induce non-stoichiometry in a given substance because the distribution of secondary element introduces equivalent vacancies in the lattice of the substance.

Optimizing a Non-stoichiometric Material

This invention enormously multiplies the number of novel substance alternatives available for producing devices and products. A preferred embodiment of this invention is to optimize the composition of the non-stoichiometric substances for best performance. Such optimization may be accomplished by methods known in the art and by parallel search approaches such as the combinatorial search method taught by us in U.S. patent application Ser. No. 09/153,418 and by U.S. Pat. No. 5,776,359, both of which are incorporated by reference herein. One embodiment is to prepare samples of non-stoichiometric materials having different compositions and to evaluate the properties of the prepared samples. The material with the best performance is selected as having the preferred composition. Another embodiment is to prepare samples of non-stoichiometric materials having different compositions, process these samples into products, and evaluate each product's performance. Finally, the nanostructured non-stoichiometric material composition that gives the best performing product is selected as the preferred composition. In yet another embodiment, a product is prepared from a non-stoichiometric substance and the non-stoichiometry varied in-situ until the performance of the product is optimized with respect to the desired specifications. Other methods may be utilized to select the best composition. In all cases, it is important to consider all possible performance, environmental, and economic requirements of the product before a selection decision is made.

While the above approaches teach how to create and produce non-stoichiometric substances, useful products can be produced from nanostructured non-stoichiometric substances by techniques and methods already known in the art. For example, if a porous body is desired, mix the non-stoichiometric powders produced as above with an inert material and reprocess the mixture. As appropriate, add a processing step which would remove the inert material using techniques such as dissolution, sublimation, evaporation, leaching, chemical reaction, or biological action. This can lead to a porous body of nanostructured form.

If a given non-stoichiometric material is expensive to prepare, one can mix the non-stoichiometric powders produced as above with a stoichiometric material and reprocess the mixture. This may help reduce the processing costs required in conversion from and to stoichiometric form.

One embodiment of this invention is to use non-stoichiometric forms of materials as precursors for combinatorial discovery of materials and related technologies such as those disclosed in our commonly assigned U.S. patent application Ser. No. 09/153,418.

Another embodiment of this invention is to prepare devices from non-stoichiometric substances. Devices can be prepared using one of the manufacturing methods used currently in the art or a combination thereof. Examples of processes which can be used at some stage include but are not limited to pressing, extrusion, molding, screen printing, tape casting, spraying, doctor blading, sputtering, vapor deposition, epitaxy, electrochemical or electrophoretic deposition, thermophoretic deposition, centrifugal forming, magnetic deposition, and stamping. The non-stoichiometric material in the device can be porous or dense, thin or thick, flat or curved, covered with a barrier or exposed. As already mentioned, with the motivation of improved performance, stable performance, reduced costs, or a combination of these, non-stoichiometric materials may be converted partially or completely into a stoichiometric form or mixed with stoichiometric materials or both after being processed into a device.

Another embodiment of this invention is to prepare a device from stoichiometric materials and then convert the stoichiometric materials into a non-stoichiometric form. For example, a ferrite device can be prepared from stoichiometric magnetic materials which can then be transformed, partially or completely, into a non-stoichiometric form by heat treating the device in borane, ammonia, hydrogen, methane, or silane to form a non-stoichiometric boride, nitride, oxide, hydride, carbide, silicide, or a combination thereof. In another example, a sensor or battery device can be prepared from stoichiometric electrochemical materials which can then be transformed, partially or completely, into a non-stoichiometric form by heat treating the device in borane, ammonia, hydrogen, methane, or silane to form a non-stoichiometric boride, nitride, oxide, hydride, carbide, silicide, or a combination thereof. In a third example, a display device can be prepared from stoichiometric photonic materials which can then be transformed, partially or completely, into a non-stoichiometric form by heat treating the device in borane, ammonia, hydrogen, methane, or silane to form a non-stoichiometric boride, nitride, oxide, hydride, carbide, silicide, or a combination thereof. In above examples in particular, and this embodiment in general, the heat treatment can be replaced by chemical methods, pressure, electrical methods, ion implantation, or any other method or combination of methods. In addition, a substrate may be incorporated into the device. While a substrate is not required for all aspects of the invention, it is required to form a structure if a device is desired. The substrate on which electrodes are formed can be flat or curved, flexible or rigid, inorganic or organic, thin or thick, porous or dense. The preferred substrates are those that provide the mechanical properties needed for device life greater than the anticipated device usage life.

In some embodiments of the presently claimed invention, it may be desirable that the device be electroded. The electrode can be a wire or plate or coil, straight or curved, smooth or rough or wavy, thin or thick, solid or hollow, and flexible or non-flexible. For some device designs, for example, bead/pellet type device designs, it is preferred that the device is formed directly on the electrode wire or plate or coil instead of on a substrate. It is important in all cases that the electrode be conductive and stable at the usage temperatures. It is preferred that the electrode composition does not react with the non-stoichiometric substance or the environment during the manufacture or use of the device. The use of nanostructured forms of non-stoichiometric materials offers the benefit of sintering temperatures for devices which are lower than the sintering temperatures achievable with coarser grained form. This may enable the use of lower cost electrode materials (e.g., copper or nickel instead of gold or platinum). It is preferred that the non-stoichiometric form is non-agglomerated and of a form that favors sintering. It is also preferred that the melting point of the electrode is higher than the highest temperature to be used during the manufacture or use of the device. One of ordinary skill in the art will realize that other device architectures can also be used in the presently claimed invention. Furthermore, non-stoichiometric form of electrodes can be utilized to improve one or more performance parameters of the electrode in the device. Some examples of non-stoichiometric electrode substances are $NiO_{1-x}$, $NiO_{1-x}N$, $NiON_{1-x}$, $Cu_2O_{1-x}$, and $PdAgO_{1-x}$. The method described in this specification for preparing non-stoichiometric ceramics may be utilized for preparing non-stoichiometric electrode as well.

The device can be produced from various non-stoichiometric compositions, including ceramics, metals and alloys, polymers, and composites. The non-stoichiometric ceramics include but are not limited to binary, ternary, quaternary, or polyatomic forms of oxides, carbides, nitrides, borides, chalcogenides, halides, silicides, and phosphides. The invention also includes non-stoichiometric forms of ceramics, undoped and doped ceramics, and different phases of the same composition.

Metals and alloys such as those formed from a combination of two or more of s group, p group, d group and f group elements may be utilized. The invention includes non-stoichiometric forms of alloys, undoped and doped metals and alloys, and different phases of the same composition. Polymers of non-stoichiometric formulations include but are not limited to those with functional groups that enhance conductivity. Specific examples include but are not limited to non-stoichiometric composites with stoichiometric polymers, defect conducting polymers, and ion-beam treated polymers. One of ordinary skill in the art will realize that other polymers, such as metal-filled polymers or conducting ceramic-filled polymers, can also be used.

Device miniaturization is also a significant breakthrough that the presently claimed invention offers through the use of nanostructured non-stoichiometric materials. Existing precursors that are used to prepare devices are based on micron-sized powders. The mass of the device depends in part on the powder size because the device thickness cannot be less than a few multiples of the precursor powder size. In a multilayer device, each layer cannot be less than a few multiples of the precursor powder size. With nanostructured powders, the active element size and therefore its mass can be reduced significantly. For example, everything else remaining the same, the mass of a device can be reduced by a factor of 1000 if 10 nanometer powders are used instead of 10 micron powders. This method of reducing mass and size is relevant to devices in the electronics, electrical, magnetic, telecommunication, biomedical, photonic, sensors, electrochemical, instruments, structural, entertainment, education, display, marker, packaging, thermal, acoustic, and other industries. The presently claimed invention teaches that nanostructured non-stoichiometric powders are preferred to reduce the mass and size of a device.

EXAMPLES

Example 1:

Processing of Materials

Densification of powders, or sintering, is essentially a process of removing the pores between the starting particles, combined with growth and strong bonding between adjacent particles. The driving force for densification is the free-energy change, or more specifically, the decrease in surface area and lowering of the free energy.

Among the processing variables that may affect the densification process, the particle size of the starting powder is one of the most important variables. In solid-state processes, assuming that the matter transport is controlled by lattice diffusion, the volume change of the material with respect to time during sintering can be related to processing variables as follows:

$$\frac{\Delta V}{V_0} = \left[3\left(\frac{20\gamma a^3 D^o}{\sqrt{2}\,kT}\right)r^{-1.2}t^{0.4}\right] \tag{5}$$

In this equation, $V_o$ and $\Delta V$ are the initial volume and volume change of the target during densification, respectively; T is the sintering temperature; t the sintering time; k the Boltzmann constant, $D^o$ the self-diffusivity, $\gamma$ the surface energy of the particle, $a^3$ the atomic volume of the diffusing vacancy, and r the radius of the particle of the starting powder.

As we can see from the above equation, the sintering time needed to achieve a specific degree of densification is proportional to the cube of the particle size of the starting powder. Given the same sintering temperature and starting material, the densification rate can be increased drastically by using 100 nm sized powders instead of 10 μm sized powders. Alternatively, to obtain the same densification or to prevent the decomposition of a fragile material at high temperatures, sintering can be conducted at lower temperature with nanostructured powders. Thus, nano-sized materials can also significantly decrease the sintering temperatures currently used for micrometer-sized powders. From a commercial viewpoint, the energy savings from lower processing temperatures and the reduction of processing times can be substantial.

Another beneficial effect of using nano-sized powders is that, because of high surface area and surface diffusivity, nano-sized composites may be sintered without impurity inducing sintering aids, resulting in more reliable sintered products which exhibit enhanced service temperatures and high temperature strength. Other anticipated benefits described below include commercially attractive processing times and temperatures, lowered inventory costs, use of lower cost precursors, and the ability to sinter devices at temperatures that prevent undesirable secondary reactions or transformations during device fabrication. While this application prefers the use of nanopowders, the teachings herein can be applied to submicron and larger non-stoichiometric powders.

For example, put the non-stoichiometric material in a die and press the material to green densities of 40% or higher. Alternatively, use injection molding, CIP, HIP, electrophoretic, magnetophoretic, coatings, gel casting, dip coating, precipitation, thick film forming, molding, screen printing, extrusion, and any of techniques known in the art to form a body from the non-stoichiometric nanopowder prepared. Next, sinter the prepared body using a temperature, time, atmosphere, and electromagnetic field sufficient to reach desired density. If desired, the sintering step may be followed by machining or processing the densified form as appropriate. Finally, transform the densified and processed non-stoichiometric structure to stoichiometric form.

The motivation of this approach is explained above and further includes the following: The stoichiometric form of $M_{n/p}Z_{1-x}$ may be given by x=0 (i.e. $M_{n/p}Z$), the lower bound case of the inequality 0<x<1. When x=1, we get the upper inequality bound and this represents the pure element M. It is known to those skilled in the art that the sintering characteristics of M and $M_{n/p}Z$ are very different. Often, M is easier to consolidate and sinter than $M_{n/p}Z$. Thus, the use of $M_{n/p}Z_{1-x}$ is anticipated to offer performance intermediate to M and $M_{n/p}Z$. From a thermodynamic point of view, the unusual interfacial free energies of non-stoichiometric forms can allow the use of more commercially attractive sintering conditions (i.e. temperature, time, field, and atmosphere) to produce the product of interest. Also, by utilizing the non-stoichiometric form $M_{n/p}Z_{1-x}$, the unusual properties of the non-stoichiometric form can be beneficially applied to produce useful objects from powders or porous bodies.

For example, in the case of Ti and $TiO_2$, the sintering temperatures for metal and metal oxide are very different. Metals are easier to sinter and process metals than ceramics.

It is expected that the sintering characteristics of a material form intermediate to the two extremes (x=0 and x=1) would also be different, in a linear or non-linear manner, than the two extremes. It is anticipated that non-stoichiometric forms of titania will be more reactive, that vacancies will assist pore volume reduction, and that these will reduce the time and temperature needed to densify a structure.

Yet another example would be to use non-stoichiometric forms of doped or undoped superconductors, ferrites, carbides, borides, nitrides, alloys, and oxides, such as NiO, $BaTiO_3$, $ZrO_2$, and hafnia. The melting point of a metal is often less than that of the corresponding ceramic form. The use of non-stoichiometric compositions can assist in achieving dense forms at lower temperatures or reduce the time needed to densify a material at a given temperature.

In some applications, the unusual properties of non-stoichiometric material may suggest that the device be used in a non-stoichiometric form. However, such devices may change their performance over time or have other disadvantages. Such problems can be addressed through the use of protective coatings, secondary phases, and stabilizers.

Dense sputtering targets of various compositions can also be prepared using the above method. These targets can then be used to prepare thin films for electronic, information storage, optics, and various other products.

The motivation to use these teachings includes commercially attractive processing times and temperatures, lowered inventory costs, use of lower cost precursors, and the ability to sinter devices at temperatures that prevent undesirable secondary reactions or transformations during device fabrication.

Example 2

Catalysis

Nanopowders comprising 75% by weight indium tin oxide (ITO) (mean grain size: 12.9 nm, 60.9 $m^2/gm$) and 25% by weight alumina (mean grain size: 4.6 nm, 56 $m^2/gm$) were mixed and pressed into pellets weighing approximately 200 mg. The pellet was reduced in a 100 ml/min 5% H–95% Ar stream at 300° C. for 10 minutes. The yellow pellet became a bluish green color. The pellet was exposed to 12% methanol vapor in air (100 ml/min) at about 250° C. and the product gases analyzed using Varian 3600 Gas Chromatograph. The gas composition analysis indicated that the product gases contained 3400 ppm of hydrogen, suggesting catalytic activity from the non-stoichiometric blue green pellet. This is in contrast with the observation that the pellet showed no catalytic activity, every thing else remaining same, when the color was yellow. The blue green pellet was replaced with a platinum wire and the temperature raised to about 250° C. No catalytic activity was detectable for the platinum wire at this temperature. These observations suggest that the non-stoichiometric indium tin oxide has unique and surprising catalytic properties when contrasted with stoichiometric indium tin oxide.

Example 3

Photonics and Optics

Stoichiometric ITO (yellow, 30 nm mean grain size) was produced via the method of commonly assigned U.S. Pat. No. 5,788,738 by feeding ITO in air. Non-stoichiometric ITO (bluish black, 30 nm mean grain size) was produced using the method of commonly assigned U.S. Pat. No. 5,788,738 by feeding ITO in forming gas (5% hydrogen–95% argon). The nanopowders were dispersed in water and the UV-Vis absorption spectra were obtained as shown in FIG. 1.

It was observed that non-stoichiometry more than doubles the absorption of infrared wavelengths. This experiment suggests that the change in stoichiometry can be used to engineer and obtain unusual optical properties of a material.

Example 4

Electrical Devices

Titanium oxide nanopowders (white, 25 nm mean grain size) were heated in ammonia for 12 hours at 600° C. The nanopowders converted to a deep blue-black color corresponding to non-stoichiometric nanopowder form (28 nm mean grain size). The electrical conductivity of the non-stoichiometric nanopowders was found to be more than ten orders of magnitude higher (resistivity of $1.5 \times 10^{-2}$ ohm-cm) than the white titanium oxide nanopowders (greater than $10^8$ ohm-cm, which is effectively insulating). Electron microscopy on the blue-black powders revealed that the nanopowders were an oxynitride of titanium ($TiON_x$). It is also of interest to note that commercially available micrometer-sized TiN powders exhibit a resistivity of about 1.5 ohm-cm, about two orders of magnitude higher than the non-stoichiometric nanopowder. Thus non-stoichiometry offers unusual non-linear properties. This example suggests the utility of non-stoichiometry and nanostructure to engineer dramatic changes in electrical properties.

Example 5

Magnetic Products

Nanoscale ferrite powders can be heated in ammonia or hydrogen or borane or methane to form non-stoichiometric ferrite. The powders can then be transformed into a form for incorporation into a device by techniques such as extrusion, tape casting, screen printing or any other methods or combination thereof.

Figure 2:
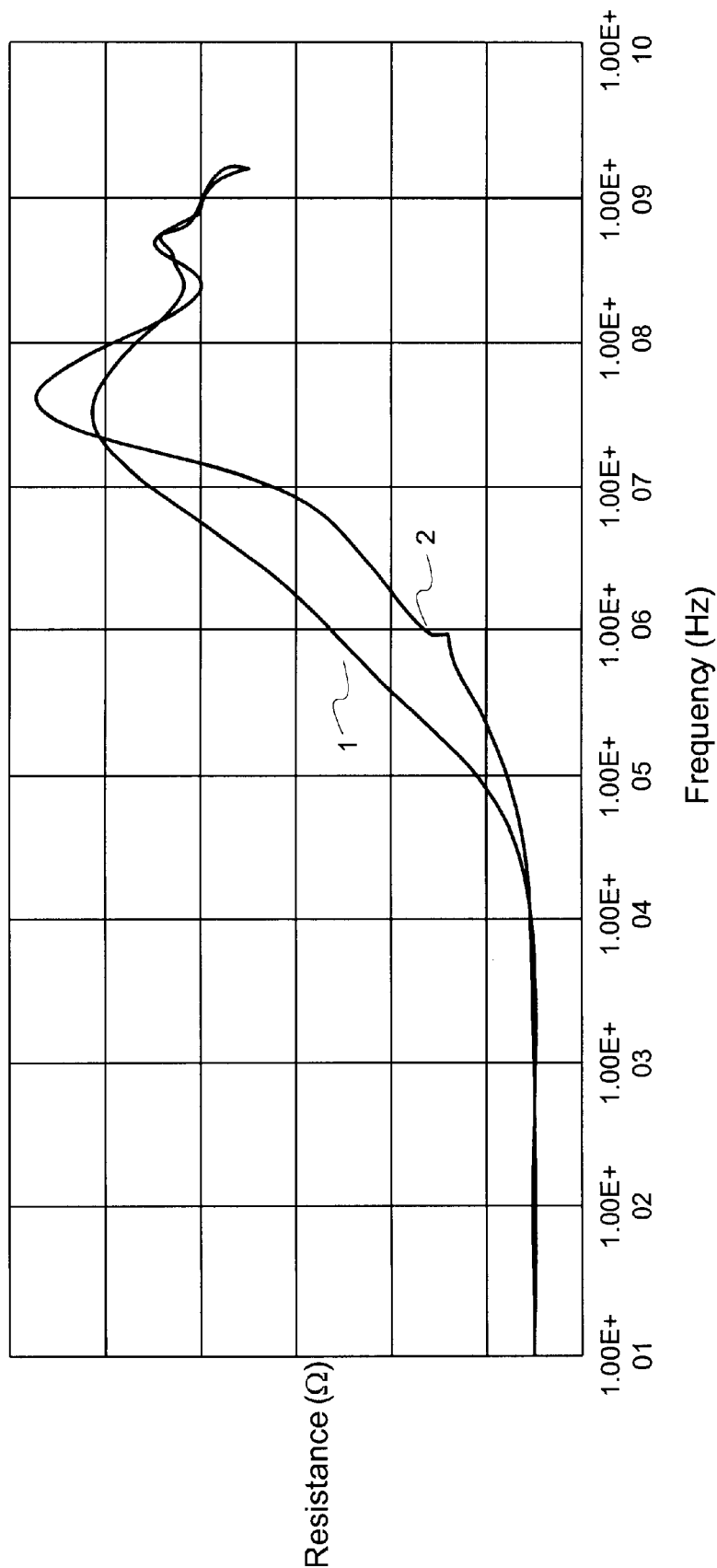
FIG. 2. Resistance of stoichiometric (1) and non-stoichiometric (2) nickel zinc ferrites as a function of frequency.

As an illustration, three toroids composed of a nickel zinc ferrite material were sintered at 900° C. for 2 hours to obtain near-theoretical densities. Upon cooling, the toroids were wound with ten turns of 26 gauge enamel-coated copper wire. Magnetic properties, including impedance, resistance, and serial inductance, were tested from 10 Hz to 1 MHz with a Quadtech 7600 LCR meter and from 1 MHz to 1.8 GHz with a Hewlett-Packard Model 4291A Analyzer. In each case, measurement consisted of making a secure contact with the stripped ends of the windings on the sample toroids and performing a frequency sweep. Once tested, the three sample toroids were unwound and heated in a reducing atmosphere. Samples were ramped from room temperature to 800° C., held for one hour, then allowed to cool. During this cycle, a stream of 5% H–95% Ar flowed continuously over the samples. Upon recovery from the furnace, a noticeable change in sample color was observed. Previously a dark gray, the "reduced" ferrite toroids now had a lighter gray, mottled appearance. The reduced ferrite toroids were rewound with ten turns of the same wire and their magnetic properties were re-evaluated. The observed results indicated a surprising change in properties in the non-stoichiometric samples: for a reference frequency of 1 MHz, the resistance increased by 732%, the inductance changed by 12.8%, and the impedance reduced by 11.4%. That dramatic changes in resistance were observed and that the overall impedance of the devices remained largely unaffected by the non-stoichiometry implies that non-stoichiometry leads to a corresponding dramatic decrease in inductive reactance. In other words, non-stoichiometric ferrite cores exhibit higher magnetic loss. FIG. 2 shows the unusual change in resistance as a function of frequency, suggesting that the non-stoichiometry is changing the fundamental performance of the materials.

Yet another method of producing a magnetic device is as follows: 900 mg of manganese ferrite non-stoichiometric nanopowder and 800 mg of nickel zinc ferrite nanopowder are pressed at 90,000 psi in a quarter inch die. For all powders, 5 wt % Duramax™ binder is added prior to pressing for improved sinterability. Pellets composed of nanopowders are sintered at 820° C. for 4 hours in a kiln with a 5° C./min ramping rate. Micrometer-sized reference pellets require sintering temperatures of 1200° C. or more for 4 hours, everything else remaining the same. After sintering, all pellet diameters are 0.6 cm, and pellet heights are about 1 cm. Each pellet is wound with 20 turns of 36 gauge enamel coated electrical wire. The final wound pellets are wrapped with Teflon tape to ensure that the windings stayed in place. These inductor samples can be characterized with an Impedance/Gain-phase Analyzer. The performance can be optimized by varying variables such as the aspect ratio, number of turns, composition, and grain size.

Example 6

Resistors and Resistor Arrays

Resistors are a mature technology and have served various industries for almost a century. They are produced in various forms and from various substances. Wire wound resistors are one of the oldest technologies used in the resistor market. The resistor is made by winding wire onto a ceramic bobbin or former. The wire materials are often alloys, and the diameter and length of the wire determine the resistivity. Metal foil resistors are prepared from metal foil that sometimes is less than one micrometer thick. The foil is stuck on a flat ceramic substrate and the resistance value engineered by precision etching a meandering pattern. These resistors are high value added and exhibit very low temperature coefficients of resistance. Film resistors are prepared by vapor deposition, anodization, or plating of metal or cermet or carbon film on a substrate, followed, if needed, by spiral cutting with a diamond wheel. Metal oxide resistors are prepared by depositing oxide vapor. Carbon film resistors are obtained by pyrolysis of hydrocarbon on ceramic substrates. Once again, spiraling is commonly used to achieve the desired resistance value. Some resistors are prepared from coating resistor inks consisting of a glass, metal particle dispersion in a viscous organic binder. The coating is stabilized by firing at temperatures around 600° C. The final resistance value is obtained by spiraling. These techniques are used for preparing discrete resistor chips, networks, or hybrid circuit systems. Desired resistance can be fine tuned by air abrasion. Conducting plastic resistors are similar to metal film oxide resistors. They differ in the fact that organic binder is here replaced with a plastic and that the dispersant is often carbon. Sintered structure resistors are prepared by sintering SiC or CrO with suitable dopants. These resistors are often used as thermistors, not as fixed linear resistors.

The presently claimed invention can be utilized in various embodiments for these devices. The composition of existing finished resistors can be transformed into non-stoichiometric forms a variety of techniques, such as heat treating (400° to 2000° C.) the device in a reducing, oxidizing, nitriding, boronizing, carburizing, or halogenating atmosphere, or a combination of these, over a period of time ranging from a few seconds to hours, shorter times being preferred.

Alternatively, existing processes to manufacture these devices may be suitably modified at an intermediate stage with one or more different processing steps to yield a non-stoichiometric form. Another embodiment of this invention is to produce nanopowders of a non-stoichiometric substance and to then substitute the substance into existing processes and process it just as one would a stoichiometric substance.

For example, 65 m$^2$/gm SiC$_{0.8}$ nanopowders were produced and sonicated in polyvinyl alcohol. The resulting dispersion was then screen printed on alumina substrate. After printing, the elements were fired at approximately 300° C. for a half hour. The resistance of the resulting device was less than 1 megaohm. Addition of platinum and silver dopants reduced the resistance further. Both p-type and n-type behavior was observed depending on the dopant.

Arrays are produced by printing multiple elements. The motivation for printing arrays is to reduce the overall product size and to reduce the cost of placing multiple elements.

Example 7

Sensor Devices

Sensors are components which sense the component's environment or changes in the component's environment. The environment may include a state of mass, energy, momentum, charge, radiation, field, electrochemistry, biological form, or a combination of one or more of these. This example discusses how the teachings in the presently claimed invention can be utilized to design and practice better performing sensors, including chemical sensors. While the teachings here describe a single layer thick film, they apply to thing film and multilayer architectures as well.

In a chemical sensor, each crystallite of the sensing material has an electron-depleted surface layer (the so-called space charge layer) having a thickness "L" around it. This length is determined by the Debye length and the chemisorbed species, and can be approximated by the following expression:

$$L = L_D \sqrt{\frac{2eV_s}{kT}} \tag{6}$$

where, $L_D$: intrinsic value of space charge thickness $eV_s$: height of Schottky barrier at grain boundaries (depends on the sort and amount of adsorbates)

k: Boltzmann's constant

T: temperature

If the crystallite size "D" is greater than twice the space charge layer thickness "L," which is always true for sensors based on existing micrometer-size grained stoichiometric materials, the electrical resistance of the sensor device is determined by the electron transport across each grain boundary, not by the bulk resistance. The resistance in this regime can be expressed as:

$$R = R_o \exp\left(\frac{eV_s}{kT}\right) \tag{7}$$

where $R_o$: bulk resistance.

The generally accepted definition of device sensitivity of a device is given by (or is a simple variation of):

$$S = \frac{R_g}{R_a} = \frac{R_o \exp\left(\frac{eV_{sg}}{kT}\right)}{R_o \exp\left(\frac{eV_{sa}}{kt}\right)} = \exp e \Delta \frac{V_s}{kT} \tag{8}$$

where, $R_a$: resistance of device in air $R_g$: resistance of device in air containing an analyte.

Because "e$\Delta V_s$" is independent of "D" until "D" is greater than twice the space charge layer thickness "L," it is no surprise that the observed sensitivity of the sensor device is independent of crystallite size in this regime. The above arguments lead to the natural question: what happens when D<2L? In this nanoscale regime, the device resistance is no longer just grain boundary controlled; instead, the bulk resistance of each grain becomes important. Since, "e$\Delta V_s$" is dependent on the adsorbate type and amount, this change in phenomenological regime provides an unprecedented way to engineer extremely sensitive sensors. In effect, one can engineer the crystallite size and the non-stoichiometry such that $R_g$ becomes bulk grain controlled (i.e., very high), while $R_a$ remains grain boundary controlled (i.e., low). This changes "e$\Delta V_s$" significantly, and since the sensitivity "S" depends exponentially on "e$\Delta V_s$," this can dramatically enhance the sensitivity of the sensor device. Enhanced sensitivity has been long sought in the sensor industry.

The benefits of nanostructured non-stoichiometric fillers may be exploited in monolithic or composite form. A composite, loosely defined, is a combination of two or more dissimilar materials, or phases, combined in such a way that each material maintains its individual character. The properties of the composite depend greatly on the arrangement of the individual phases present. In completely homogeneous composites, the properties tend to be a combination of the properties of the distinct phases present, a combination that is often unobtainable with metals, ceramics, or polymers alone. This makes composites unique and very appealing for applications which require a demanding and conflicting matrix of design needs. Sensors are one such application where conventional materials in monolithic form often excel in meeting some design goals, but fail to meet others. Composites of nanoscale non-stoichiometric substances can potentially provide the breakthrough where all the needs are simultaneously met. This embodiment is particularly useful when the selectivity of the sensor needs improvement.

Sensors (and sensor arrays) can prepared by numerous methods and the benefits of nanoscale non-stoichiometric substances can be practiced with any of these methods. In one embodiment, sensing films were prepared by brushing on a slurry containing nanoscale non-stoichiometric powders (and polymer, if appropriate) onto a screen-printed electrode on a substrate. The sensor electrodes were prepared using a Presco Model 465 Semi-Automatic Screen Printer. This equipment facilitated automatic printing, with the exception of loading and unloading the substrate. The screen used was from Utz Engineering, Inc. The screen was made from stainless steel mesh and had a frame size of 8×10 inches, a mesh count of 400, a wire diameter of 0.0007 inches, a bias of 45 degrees, and a polymeric emulsion of 0.0002 inches. The gold electrodes were screen printed on a 96% alumina substrate and then fired in air at 850° C. for a peak time of 12 minutes. Dopant polymers were dissolved in an appropriate solvent. Once the polymer was dissolved, non-stoichiometric nanopowders were added to the solution and sonicated for 20 minutes. The slurry was then deposited onto an electrode using a small paint brush. Once deposited, the elements were allowed to dry in air at 100° C. for 30 minutes to remove the solvent.

In an alternate embodiment, a screen printable paste was first prepared. The paste was again prepared from nanopowder and polymer. The nanopowder, polymer, and catalyst (when included) were weighed out and mixed together in a mortar and pestle. Next, screen printing vehicle was weighed out and transferred to the mortar and pestle where the two phases were mixed together. Finally, this paste was placed on a three roll mill and milled for five minutes. The three roll mill allowed for high shear mixing to thoroughly mix the paste and to break up agglomerates in the starting nanopowder. After the paste was prepared it is screen printed on to the prepared electrodes, allowed to level, and then dried at 100° C. This embodiment illustrates a method for preparing single elements and arrays of sensors.

Next, the sensing elements were screened, tested, and optimized for sensitivity, selectivity, and response time, as described below.

The sensitivity is calculated from the change in resistance of the sensor when exposed to a background and when exposed a vapor analyte species in background and determines the threshold exposure levels. A simple variation of the above equation describing sensitivity is:

$$Sensitivity = \frac{R_a - R_s}{R_s} \quad (9)$$

where:

$R_a$=sensor resistance in background $R_a$=sensor resistance when exposed to analyte vapor.

The selectivity is a comparison of either the sensitivity of an individual sensor to two different analytes or of two sensors to the same analyte.

$$Selectivity = \frac{Sensitivity_a}{Sensitivity_b}$$

The response time is the time it takes for the sensor to detect a change in the surrounding environment, defined as the time required for the sensor to reach 90% of its peak resistance ($R_s$).

With non-stoichiometric nanoscale powders, low temperature sensing elements with sensitivity S greater than 1.5, selectivity greater than 1.1, and response times less than 10 minutes can be obtained for wide range of gaseous and liquid analytes. With optimization, selectivity greater than 2, sensitivity greater than 1.5, and response time less than 1 minute can be obtained at ambient conditions.

Some specific examples of analytes that can be sensed using the teachings herein, include, but are not limited to: carbon oxides (CO, $CO_2$), nitrogen oxides ($NO_x$), ammonia, hydrogen sulfide, borane, hydrogen, hydrazine, acidic vapors, alkaline vapors, ozone, oxygen, silane, silicon compounds, halogenated compounds, hydrocarbons, organic compounds, organometallic compounds, metal vapors, and volatile inorganics.

Example 8

Biomedical Products

Mechanical alloying can be used to prepare nanocrystalline non-stoichiometric alloys. The feed powder Ti-4.9Ta-11Nb-15.2Zr is loaded in non-stoichiometric proportions into a cylindrical hardened steel vial with hardened steel mill balls. The ball-to-powder ratio is preferably high (5:1). The loading process is preferably done within an argon atmosphere glove box. The environment inside is maintained at an oxygen concentration of <100 PPM and moisture content of <3.0 PPM. The mill itself is set up outside of the glove box and the vial and mill housing cooled using forced air convection. After milling, the vial is transferred back to the glove box where the non-stoichiometric powder is collected and submitted for analysis or further processing. To prepare an orthopedic implant, the synthesized powders are uniaxially pressed. Poly(ethylene glycol) (PEG) may be used as a binder for compaction of the powders. PEG is added to the powders by preparing a 1 weight percent solution in ethanol and wet mixing the solution with the alloyed powders. The homogeneous mixture is air dried at room temperature. A press can be used to compact the powders in a die. A uniaxial 11,250 lb. force is applied (resulting in 225,000 psi of pressure) which is appropriate for implant specimens.

One advantage of non-stoichiometric nanoscale powders is the potential use of non-toxic elements in orthopedic and other biomedical implants. In general, biomedical implants are engineered to control properties such as strength, toughness, modulus, corrosion resistance, biocompatibility, porosity, surface roughness, and wear resistance. The materials described in the previous paragraph can be optimized to match the modulus of bone, a desirable characteristic of materials for some joint replacement applications. In other embodiments, nanopowders can be utilized for drug delivery and as markers for diagnosis. Nanopowders can also be utilized for enhancing the solubility of drugs in organic and inorganic solvents. In yet other embodiments, the teachings can be applied to various products where inorganic and organic powders are currently being utilized, as known to those skilled in the art.

Example 9

Electronic Components

Electronic components, for example, disc and multilayer capacitors, inductors, resistors, filters, antennas, piezoelectric devices, LED, sensors, connectors, varistors, thermistors, transformers, current converters, shields, or arrays of such components in conventional mount or surface mount form, can be prepared using the teachings herein. As an example, to prepare varistors from nanoscale non-stoichiometric materials, a paste of the powders was prepared by mixing the powder and screen printing vehicle with a glass stir rod. Exemplary compositions include $ZnO_{1-x}$, $Bi_{2/3}O$, and other oxides. Silver-palladium was used as the conducting electrode material. A screen with a rectangular array pattern was used to print the paste on an alumina substrate. The process consists of screen printing the electrode and rapidly drying the film on a heated plate. The process was attended and precautions taken to prevent electrically shorting the device. The final electrode was applied in the same manner as the first. The effective non-stoichiometric nanostructured-filler based composite area in the device due to the offset of the electrodes was small (0.2315 cm$^2$). However, this offset may be increased or further decreased to suit the needs of the application. The thick green films were co-fired at 900° C. for 60 minutes.

Such a device offers a means to control surge voltages. An accurate determination of device non-linearity, α, can be obtained using the empirical varistor power law equation:

$$I = nV^\alpha \quad (11)$$

where:

I=current.

n=the varistor power coefficient.

V=voltage.

The value of α obtained for the nanostructured non-stoichiometric device is anticipated to be 10 fold higher than that achievable with micrometer-sized stoichiometric fillers. It is also expected that the resistance of the boundaries would be lower, enabling clamping capability of lower voltages and higher frequencies. Other components that can specifically benefit from the high surface area of nanostructured non-stoichiometric materials include but are not limited to positive temperature coefficient resistors and barrier layer capacitors.

Example 10

Electrochemical Products

Electrochemical products, for example, batteries, electrolytic cells, corrosion inhibitors, electrodes in metallurgical applications and other industries, pH sensors, and electrochemical sensors, can benefit from the use of non-stoichiometric nanopowders. The most distinctive feature of these non-stoichiometric nanopowder materials is their unique thermodynamic state and the large number of atoms situated in the interfaces. A 10 nm nanocrystalline metal particle contains typically $10^{25}$ atoms which are situated on or near the interface per cubic meter of material; thus, 30% of total atoms in the material are situated in the interfaces or on the surface and exhibit non-bulk properties. Such a unique ultra-fine structure of nanopowders, when applied to electrochemical products, can lead to a drastic improvement of their performance. The ultra-fine (nanometer scale) microstructure of nanostructured hydrogen storage materials, to illustrate, will not only enhance the thermodynamics and kinetics of hydriding and dehydriding processes, but also improve their structure stability, and thus reliability and life time.

Particularly, nanostructured materials offer the following motivation for their utilization:

(i) Drastic Increase of Species Solubility or Capacity

The ultra-fine grain size of nanostructured materials gives an excess Gibbs free energy to the system compared to the conventional large grained (micrometer size) hydrides. This will significantly enhance the solubility of solute atoms, including hydrogen, because:

$$\frac{C_d}{C_\infty} = \frac{kV}{RT}\frac{\sigma}{d} \tag{12}$$

where:

$C_d$ and $C_\infty$=solubilities of a solute in the material with average grain size d and infinite grain size, respectively;

R=gas constant;

T=temperature;

V=the molar volume of the solute;

k=Boltzmann's constant;

σ=the surface energy of the grain.

Thus, theoretically, a 10 nm grained hydride is expected to have a hydrogen solubility 1000 times higher than a 10 μm grained hydride with the same chemical composition. The use of non-stoichiometric nanoscale powders offers to further enhance the thermodynamic and/or kinetic potential of the system. Other advantages of non-stoichiometric formulations, for example, faster and more economical processing conditions, still apply.

(ii) Significant Enhancement of Hydrogen Diffusivity

The large volume fraction of interface in nanostructured materials will result in grain boundary diffusion dominating the overall diffusion in the materials. The overall or effective diffusivity of solute atoms in the material is given by:

$$D^{eff}=fD_{gb}+(1-f)D_{lt} \tag{13}$$

where:

$D^{eff}$=the effective or overall diffusion coefficient;

$D_{gb}$=the diffusion coefficient in grain boundaries;

$D_{lt}$=the diffusion coefficient within grains.

f=the fraction of solute atoms on the grain boundaries. Since $D_{gb}$ normally is $10^4$ times higher than $D_{lt}$, or $D_{gb}>>D_{lt}$, and more than 30% of atoms are situated in the grain boundaries, the above equation can be rewritten as $$D^{eff} \approx fD_{gb}=0.3D_{gb}>>D_{lt} \tag{14}$$

The solute diffusion coefficient in nanostructured materials, therefore, is expected to be 1000 to 10,000 times higher than in conventional micro-grained materials.

(iii) Reduction of Temperature and Pressure for Hydride Formation and Dissociation The excess free Gibbs energy due to the ultra-fine structure of nanomaterials will also lead to significant change in phase transformation temperatures such as the hydride formation temperature. The phase transformation temperature change ΔT due to the ultrafine structure is related to the grain size d by:

$$\Delta T = \frac{(\sigma_1 - \sigma_2)T_c}{L}\frac{k}{d} \tag{15}$$

where:

$\sigma_1,\sigma_2$=specific surface energies of phase 1 and phase 2, respectively;

L=the heat of transformation from phase 1 to phase 2;

$T_c$=the phase transformation for the bulk material;

k=Boltzmann's constant.

Thus, the phase transformation temperature is expected to change as the grain size decreases. Because the hydrogen dissociation pressure decreases as the dissociation temperature decreases, the ultra-fine microstructure of nanostructured materials in general, and non-stoichiometric nanomaterials in particular, is preferable design guideline to a lower hydrogen dissociation pressure. This is very desirable in hydrogen storage technologies. This basic guideline for practice applies even to other electrochemical couples and systems such as batteries and electrodes. The benefits of lower phase transformation temperature have utility beyond electrochemical products and apply to thermal (e.g. heat transfer fluids) and other applications as well.

(iv) Higher Resistance to Pulverization During Hydriding/Dehydriding Processes

High strength is essential to pulverization resistance due to large lattice expansion and contraction during hydriding/dehydriding processes. The ultrafine grain size of nanostructured hydrides offers a drastic improvement in their structure stability. This can be inferred from the yield strength of a material which is related to its grain size d by the Hall-Petch relationship:

$$\sigma_y = \sigma_o + \frac{k_y}{\sqrt{d}} \tag{16}$$

Fracture toughness, $K_{1c}$, is related to grain size by:

$$K_{1c}=\sigma_y\sqrt{\pi\alpha_c} \tag{17}$$

where:

$\sigma_y$=the yield strength;

$\sigma_o$=the frictional stress needed to move the dislocation;

$k_y$ = a constant;

$a_c$ = the critical crack length.

This indicates that as the grain size decreases from 10 µm to 10 nm, both the strength and fracture toughness are expected to increase by a factor of 30, which in turn leads to a higher resistance to pulverization. Thus, electrochemical products in particular, and other products in general, can benefit from superior performance of nanostructured materials.

Some specific examples for the use of non-stoichiometric nanomaterials in electrochemical products would be rare-earth doped or undoped $Mg_{1.8}Ni$, $Ni\text{—}ZrNi_{1.6}$, $La_{0.9}Ni_5$, and other existing compositions with non-stoichiometry as explained previously.

Example 11

Energy and Ion Conducting Devices

Stoichiometric nanoscale 9 mole % yttria-stabilized cubic zirconia powders ($Y_{18}Zr_{91}O_{209}$) are first reduced at moderate temperatures (500° to 1200° C.) in a forming, or reactive, gas to yield non-stoichiometric $Y_{18}Zr_{91}O_{185}$ nanopowders. These powders are pressed into 3 mm diameter discs and then sintered to high densities. The disks should be preferably sintered at low temperatures (preferably 800° to 1200° C.) for short times (preferably 6 to 24 hours) to minimize grain growth. These nanopowders, as discussed before, can be readily sintered to full theoretical densities (99% or more). Careful control and optimization of the sintering profile and time can reduce the sintering temperature and time further. The two ends of the cylindrical discs so produced are then coated with a cermet paste consisting of a mix of silver and nanoscale stoichiometric yttria stabilized zirconia powder (a 50–50 wt % mix). Non-stoichiometric nanoscale powders can be utilized in the electrode as well. Platinum leads are then attached to the cermet layer. This device can serve as an oxygen-conducting electrolyte with significantly higher oxygen ion conductivity at lower temperatures than conventional electrolytes. Exemplary devices include but are not limited to oxygen sensors, oxygen pumps, or fuel cells. In this example, the degree of non-stoichiometry is arbitrarily chosen, and further optimization can be beneficial to the economics and performance.

The benefits of this invention can be utilized even when the yttria in the zirconia formulation is replaced with other stabilizers such as scandium oxide, calcium oxide, and other oxides. Similarly, other Group IV oxides (e.g. ceria) and perovskites can be used instead of zirconia. Other ion conductors, for example, beta alumina and NASICONs for sodium ion, lithium nitride and LISICONs for lithium ions, silver iodide for silver ions, $Rb_4Cu_{16}I_7Cl_{13}$ for copper ions, polymers such as nafion and perovskites for hydrogen protons, can all benefit from the use of non-stoichiometry in the ion conducting electrolytes and/or electrodes.

Example 12

Dopants in Formulations and Inks

Often, it is necessary to add secondary phase particles to a primary powder element to achieve a desired property, such as temperature coefficient of the dielectric constant. For example, commercial capacitor formulations of the Electronic Industry of America (EIA) X7R designation contain additions of dopants (e.g. tantalum oxide, niobium oxide, nickel oxide, bismuth oxide, silicates, titanates, and manganese oxide) which are added to the base barium titanate powder to tailor the temperature-capacitance or other characteristics of the material. The secondary phase particle additions are also often used to facilitate low temperature sintering. These materials include, but are not limited to, bismuth oxide, copper oxide, titanium oxide, silicon oxide, and vanadium oxide.

In these powder mixtures, it is usually desirable to achieve a uniform mixture of the primary phase particles and the secondary phase particles. This can be difficult if the volume fraction of the secondary particles is small and if the size of the secondary particles is large in relation to that of the primary particles. The problem is that the number fraction of the secondary particle phase is small in relation to that of the primary particle phase; thus, the relative distances between the secondary phase particles can be rather large. This can translate to a non-uniform distribution of the secondary phase particle species throughout the powder element and also in the microstructure of the final product.

Nanocrystalline powders in general and non-stoichiometric powders in particular produced by any technique can reduce the size of the secondary particles relative to primary particles and in turn, increase the number fraction of the secondary particles in the powder element. This will translate to a uniform mixedness in the powder element and in the product's microstructure.

To illustrate, 80 run (preferably 40 nm, more preferably 10 nm) $Ta_{2/3}O_{0.9}$, $Nb_{2/5}O_{0.74}$, $NiO_{0.98}$, $Mn_{1/2}O_{0.9}$, $Bi_{2/3}O_{4.5}$, $Cu_{1.9}O$, $TiO_{1.1}$, $SiO_{1.55}$, and $V_{2/5}O_{0.975}$ are examples of non-stoichiometric nanopowders that can be used as dopants in device formulations and inks.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A submicron non-stoichiometric material, wherein the value for a selected physical property of the submicron non-stoichiometric material is greater than 5% different from that for a thermodynamically equilibrium form of the submicron non-stoichiometric material.

2. The submicron non-stoichiometric material of claim 1, wherein the selected physical property is an electrical property.

3. The submicron non-stoichiometric material of claim 1, wherein the selected physical property is a catalytic property.

4. The submicron non-stoichiometric material of claim 1, wherein the selected physical property is an optical property.

5. The submicron non-stoichiometric material of claim 1, wherein the selected physical property is an electrochemical property.

6. A submicron non-stoichiometric material, wherein relative ratios of components of the submicron non-stoichiometric material differ by more than 1% from thermodynamically equilibrium form of the submicron non-stoichiometric material.

7. The submicron non-stoichiometric material of claim 6, wherein the relative ratios of the components of the material differ by more than 2% from the stoichiometric values.

8. The submicron non-stoichiometric material of claim 6, wherein the relative ratios of the components of the material differ by more than 5% from the stoichiometric values.

9. The submicron non-stoichiometric material of claim 6, wherein the material is a nanomaterial.

10. The submicron non-stoichiometric material of claim 6, wherein the material is a nanopowder.

11. A submicron material, wherein
a domain size of the submicron material is less than 500 nm, and the submicron material is a non-equilibrium non-stoichiometric material.

12. The submicron material of claim 11, wherein the domain size is less than 100 nm.

13. The submicron material of claim 11, wherein the submicron material is a nanostructured material.

14. The submicron material of claim 13, wherein the material contains oxygen.

15. The submicron material of claim 13, wherein the material contains nitrogen.

16. The submicron material of claim 13, wherein the material contains boron.

17. The submicron material of claim 13, wherein the material contains carbon.

18. The submicron material of claim 13, wherein the material contains hydrogen.

19. The submicron material of claim 13, wherein the material contains halogen.

20. The submicron material of claim 13, wherein the material contains chalcogen.

21. The submicron material of claim 13, wherein the material contains at least two metals.

22. The submicron material of claim 11, wherein the material is a powder.

23. The submicron material of claim 22, wherein the material is nanopowder.

24. A nanostructured material useful in an application, wherein:
a domain size of the nanostructured material is less than 500 nm;
the nanostructured material is non-equilibrium and non-stoichiometric; and
a selected property representative of the application in the nanostructured material is greater than 5% different from that for a stoichiometric form of the nanostructured material.

25. The nanostructured material of claim 24, wherein the application is a catalytic application.

26. The nanostructured material of claim 24, wherein the application is an optical application.

27. The nanostructured material of claim 24, wherein the application is a biomedical application.

28. The nanostructured material of claim 24, wherein the application is a battery.

29. The nanostructured material of claim 24, wherein the application is a fuel application.

30. The nanostructured material of claim 24, wherein the application is a magnetic application.

31. The nanostructured material of claim 24, wherein the application is an application from the group comprising of carrier, marker, drug delivery application.

32. The nanostructured material of claim 24, wherein the application is a structural application.

33. The nanostructured material of claim 24, wherein the application is a sensing application.

34. The nanostructured material of claim 24, wherein the application is a hydrogen storage application.

35. A nanostructured material useful in an application, wherein a domain size of the nanostructured material is less than 500 nm, the nanostructured material is non-equilibrium and non-stoichiometric, and the nanostructured material is produced by heating.

36. The nanostructured material of claim 35, wherein the application is a catalytic application.

37. The nanostructured material of claim 35, wherein the application is an optical application.

38. The nanostructured material of claim 35, wherein the application is a biomedical application .

39. The nanostructured material of claim 35, wherein the application is a battery.

40. The nanostructured material of claim 35, wherein the application is a fuel application.

41. The nanostructured material of claim 35, wherein the application is a magnetic application.

42. The nanostructured material of claim 35, wherein the application is an application from the group comprising of carrier, marker, drug delivery application.

43. The nanostructured material of claim 35, wherein the application is a structural application.

44. The nanostructured material of claim 35, wherein the application is a sensing application.

45. The nanostructured material of claim 35, wherein the application is a hydrogen storage application.

* * * * *